US009744256B2

(12) United States Patent
Gschwind et al.

(10) Patent No.: US 9,744,256 B2
(45) Date of Patent: Aug. 29, 2017

(54) NEBULIZER SYSTEM FOR FRESHENING THE AIR

(71) Applicant: ARECO FINANCES ET TECHNOLOGIE—ARFITEC, Grasse (FR)

(72) Inventors: Michel Gschwind, Placassier (FR); Frédéric Richard, Golfe Juan (FR); Abbas Sabraoui, Grasse (FR)

(73) Assignee: Areco Finances et Technologie-Arfitec, Grasse (FR)

(*) Notice: Subject to any disclaimer, the term of this patent is extended or adjusted under 35 U.S.C. 154(b) by 166 days.

(21) Appl. No.: 14/888,190

(22) PCT Filed: Apr. 29, 2014

(86) PCT No.: PCT/FR2014/051025
§ 371 (c)(1),
(2) Date: Oct. 30, 2015

(87) PCT Pub. No.: WO2014/177805
PCT Pub. Date: Nov. 6, 2014

(65) Prior Publication Data

US 2016/0067368 A1 Mar. 10, 2016

(30) Foreign Application Priority Data

Apr. 30, 2013 (FR) ..................................... 13 53966

(51) Int. Cl.
*B64D 1/00* (2006.01)
*A61L 9/14* (2006.01)
(Continued)

(52) U.S. Cl.
CPC ................ *A61L 9/14* (2013.01); *A47F 3/001* (2013.01); *B05B 7/0012* (2013.01);
(Continued)

(58) Field of Classification Search
CPC ....... A61L 9/14; B05B 17/06; B05B 17/0607; B05B 12/087081; B05B 12/082
(Continued)

(56) References Cited

U.S. PATENT DOCUMENTS 3,851,333 A * 11/1974 Fishman ............. G01F 23/2961
137/487.5
4,054,622 A * 10/1977 Lester .................... A61M 11/06
128/200.13
(Continued)

FOREIGN PATENT DOCUMENTS

EP 0691162 A1 1/1996
EP 0931595 A1 7/1999
(Continued)

*Primary Examiner* — Arthur O Hall
*Assistant Examiner* — Viet Le
(74) *Attorney, Agent, or Firm* — Jordan IP Law, LLC; Todd A. Vaughn

(57) ABSTRACT

Nebulizer systems to generate a mist of micro-droplets of a liquid for the purpose of freshening the atmosphere. Nebulizer systems having a small size that can be mounted on a sales stall to humidify and freshen fresh products displayed for sale, or in a vehicle to humidify and freshen the air and make it pleasant to breathe.

18 Claims, 7 Drawing Sheets

Figure 1A:
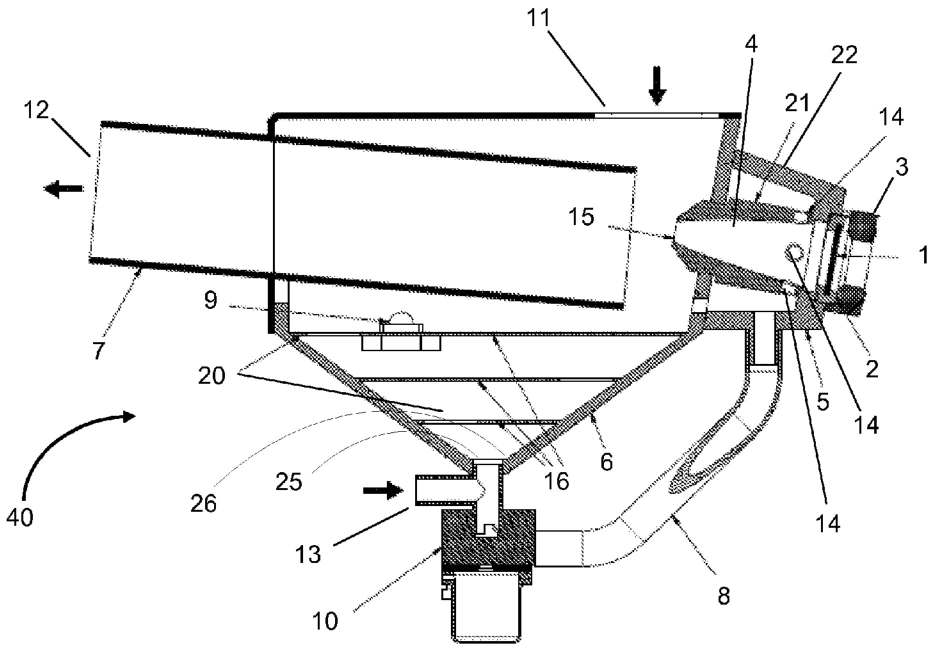

(51) Int. Cl.

| | |
|---|---|
| ***A47F 3/00*** | (2006.01) |
| ***B05B 7/00*** | (2006.01) |
| ***B05B 17/06*** | (2006.01) |
| ***B60H 1/32*** | (2006.01) |
| ***F24F 6/14*** | (2006.01) |
| *B05B 12/08* | (2006.01) |
| *B64D 13/06* | (2006.01) |
| *F24F 6/00* | (2006.01) |

(52) U.S. Cl.
CPC ...... *B05B 17/0607* (2013.01); *B05B 17/0676* (2013.01); *B60H 1/32* (2013.01); *F24F 6/14* (2013.01); *B05B 12/08* (2013.01); *B05B 12/081* (2013.01); *B05B 12/082* (2013.01); *B64D 2013/0662* (2013.01); *F24F 2006/008* (2013.01); *Y02B 30/545* (2013.01)

(58) Field of Classification Search
USPC .................................................. 239/20, 102.2
See application file for complete search history.

(56) References Cited

U.S. PATENT DOCUMENTS

| | | | | |
|---|---|---|---|---|
| 4,257,989 | A * | 3/1981 | Nishikawa | B01J 47/14 210/282 |
| 4,702,418 | A * | 10/1987 | Carter | A61L 9/14 239/101 |
| 2008/0283626 | A1* | 11/2008 | Aldana | A61L 2/22 239/68 |
| 2012/0251296 | A1* | 10/2012 | Jorgensen | B05B 17/0676 415/116 |

FOREIGN PATENT DOCUMENTS

| | | | |
|---|---|---|---|
| FR | 2716415 | A1 | 8/1995 |
| FR | 2743313 | A1 | 7/1997 |
| FR | 2787352 | A1 * | 6/2000 |
| FR | 2788706 | A1 | 7/2000 |

* cited by examiner

NEBULIZER SYSTEM FOR FRESHENING THE AIR

CROSS-REFERENCE TO RELATED APPLICATIONS

The present application is a National Stage Application of PCT International Application No. PCT/FR2014/051025 (filed on Apr. 29, 2014), under 35 U.S.C. §371, which claims priority to French Patent Application No. 1353966 (filed on Apr. 30, 2013), which are each hereby incorporated by reference in their respective entireties.

TECHNICAL FIELD

The invention relates to nebulizer systems able to generate a mist of micro-droplets of a liquid, for example water, for the purpose of freshening the atmosphere, and more particularly nebulizer systems of small size that can be mounted on a sales stall to humidify and freshen fresh products displayed for sale, or in a vehicle to humidify and freshen the air and make it pleasant to breathe.

BACKGROUND

Such systems are known as such. Patent EP 0 691 162 describes a nebulizer system with a concentration nozzle wherein a piezoelectric component immersed in the water generates a mist of droplets of water at the outlet of a nozzle which concentrates the ultrasounds generated by said piezoelectric component at its outlet point; the mist is then conveyed by an air current generated by a fan. This nozzle is generally arranged vertically, with the focalizing outlet pointing upwards; the nozzle can also be inclined, for example at 45°.

Such systems are commonly used on stalls for selling fresh products; this normally corresponds to a stationary and stable environment. On the other hand, no use is known in vehicles, which have a non-stationary and disturbed environment. Moreover, the systems used on stalls can be improved in that a stall itself can also be disturbed by impacts and other mechanical disturbances, because it is surrounded by persons who can come into mechanical contact with it.

More particularly, the mechanical disturbances can generate a fluctuation in the supply with water of the concentration nozzle. However, if the piezoelectric component is not constantly immersed during its operation it can be damaged.

The applicant noticed that the constructive measures that aim to reduce the encumbrance of the system, and in particular its height, tend to increase the risk that the piezoelectric component be found temporarily incompletely immersed or even dry. More particularly, it is observed that when it is sought to incline the nozzle, which participates in decreasing the overall height of the system, the operation of the system is less resistant to mechanical disturbances than in the case of a vertical nozzle. Likewise, when it is sought to decrease the total quantity of water in the system, which participates in decreasing the overall encumbrance of the system, there is an increase in the risk of a lack of water in the nozzle.

SUMMARY

This invention constitutes an improvement of this system, in particular for its use in environments disturbed by movement, acceleration, vibration or impact, and in particular in vehicles.

More precisely, the purpose of the invention is to present a nebulizer device that is compact, robust, reliable and simple to use, lightweight and inexpensive, that can be used to humidify, freshen and/or perfume and/or disinfect the air of the passenger compartment of a vehicle.

Another purpose is to present a nebulizer device that is compact, robust, reliable and simple to use, lightweight and inexpensive, that can be used to humidify or freshen merchandise, in particular fresh products, displayed for sale on a stall. Yet another purpose is to present a nebulizer device that is compact, robust, reliable and simple to use, lightweight and inexpensive, that can be used to humidify, freshen and/or perfume and/or disinfect the air of a stationary premises, such as a workshop, and in particular in mechanically disturbed conditions, for example by vibrations or impacts.

The requirement concerning compactness is the result of the need of a general small size for the device, and in particular a limited height, which is particularly strong when the device has to be integrated into a vehicle passenger compartment.

The requirement concerning robustness is the result of the need of resistance of the device against disturbed conditions, and of its reliable operation in disturbed conditions, such as slopes, sudden acceleration and braking, vibrations, impacts. It is also the result of the desire to avoid frequent maintenance of the nebulizer.

The requirement concerning simplicity of use results in particular from the practical impossibility of asking the user to makes sure that the nebulizer has a regular supply of water.

The requirement concerning lightness is the result of the general need to limit the weight that is added to a vehicle (and in particular to an aircraft) by the adding of additional options and functions.

The requirement concerning price works in favor of a device with a simple construction.

These objectives are achieved by a nebulizer device that is able to generate and diffuse a mist of micro-droplets in order to freshen and/or humidify the ambient atmosphere of a premises and/or in order to freshen and/or humidify products exhibited on a sales display case, and/or to freshen and/or perfume the atmosphere of a passenger compartment, said device comprising:

(a) a nebulizer nozzle provided with at least one opening for the intake of liquid and with at least one liquid-outlet opening, and on the side opposite said outlet opening a piezoelectric component which can emit acoustic waves into the liquid, and the transversal section of said nozzle having a progressive narrowing in the direction of said first outlet opening, in such a way that in said nozzle the acoustic waves are focused in order to create a mist of droplets of said liquid;

(b) a collection reservoir which supplies said nozzle with liquid, (c) a pump referred to as "circulation pump" connected on the one hand to the collection reservoir and on the other hand to said nozzle by the at least one intake opening provided in said nozzle, said circulation pump being able to generate in said nozzle a liquid pressure sufficient to maintain a liquid jet emerging via said outlet opening of the nozzle, (d) a pressurizing chamber through which passes the liquid emerging from the circulation pump before entering said nozzle, said nebulizer device being characterized in that the volume of the upper part of the pressurizing chamber at a liquid level which is higher than the highest of the following three points: the opening for the intake of water of the highest nozzle, the upper edge of the outlet opening of the nozzle, the highest point of the ceramic component, is at least twice (preferably at least six or even more preferably at least twelve times) as large as the volume of the nozzle. This nebulizer device forms the first object of the invention. It can be carried out according to various embodiments and alternatives.

The section of intake of the nozzle (i.e. the sum of the surfaces of the intake openings) must be higher than the section of the outlet opening, and preferably at least three times higher, in order to prevent the phenomenon of cavitation in the nozzle.

As such, the device according to the invention has a V5/V4 ratio and a sizing of the outlet opening of the nozzle and openings for the intake of liquid of the nozzle such that when the circulation pump ceases to provide water, the piezoelectric component remains immersed in said liquid (and could as such continue to operate without risk of damage) for a period is which is advantageously at least one second and preferably between 1 and 10 seconds, and preferably between 2 and 5 seconds.

Thanks to its nozzle that focuses acoustic waves generated by a piezoelectric component, the nebulizer device according to the invention is able to create and diffuse a mist formed of droplets of a typical average diameter between 0.5 μm and 10 μm, preferably between 1 μm and 5 μm.

The focusing of the acoustic waves will be more effective in creating a mist of droplets of said liquid if the progressive narrowing of the transversal section of said nozzle in the direction of said first outlet opening is such that the acoustic waves are focused on said outlet opening. The focusing will be done advantageously in the longitudinal axis of the nozzle which passes through the center of the outlet opening, and further advantageously in the horizontal plane of said opening or slightly outside of this plane.

Said liquid to be nebulized is preferably water, which can comprise additives, such as perfumes and/or disinfecting products (for example: H2O2, peracetic acid, citric acid).

The device according to the invention comprises advantageously means of ventilation for creating a flow of air that carries said mist of droplets towards the exterior of said device.

Generally, said circulation pump can be of any suitable type; a propeller pump is suitable. It is advantageously located below the collection reservoir.

In an embodiment of the device according to the invention, said collection reservoir comprises at least one plate for stabilizing the level of liquid, arranged horizontally, vertically or at an angle, each comprising at least one opening. This secures the supplying of the circulation pump with liquid, stabilizes the liquid jet and makes the operation of the device reliable.

Advantageously, said stabilization plates are of a number of at least two and are arranged in such a way that the openings are offset in relation to one another. This improves their stabilization effect of the level of liquid in the collection reservoir. Alternatively or in addition, at least one portion of said openings can be shut off by a valve which opens at least partially under a water pressure coming from one side and closes under a water pressure coming from the other side, or opens not as widely under a water pressure coming from one side as under an equivalent water pressure coming from the other side.

In another embodiment, at least one of said stabilization plates is carried out at least partially in the form of a grille or strainer.

Another means to make the operation of the device insensitive to the mechanical disturbances consists of a specific construction of the bottom of said collection reservoir, which is inclined in the direction of a discharge opening through which the liquid enters into said circulation pump. In an alternative embodiment, the collection reservoir has the shape of a funnel.

In an embodiment that can be combined with all of the others, the longitudinal axis of said nozzle forms an angle of inclination $\alpha$ with respect to the horizontal which is between 0° and 45°, preferably between 0° and 30° and even more preferably between 5° and 20°. This allows for a construction of the device that is particularly compact.

The device can comprise a collection tube able and arranged to collect the liquid jet emerging from the outlet opening and to empty into said collection reservoir. It can be inclined in relation to the vertical. This collection tube can be passed through by said flow of air, that carries said mist of droplets towards its outlet. This decreases the height of the device and simplifies its construction.

In an embodiment that can be combined with the preceding ones, the collection reservoir and said nozzle form a single bloc.

In another embodiment that can be combined with the preceding ones, the device comprises a secondary liquid reservoir connected to the primary reservoir, said secondary reservoir being more preferably a flexible or semi-rigid reservoir. It supplies, permanently or intermittently, said collection reservoir, more preferably through the intermediary of a pump.

In an embodiment that can be combined with the preceding one or with all of the others, the nebulizer system according to the invention is supplied with water by a system for recovering water coming from outside of said nebulizer system. This recovered water can be water from the condensation that forms on surfaces of materials in contact with the ice melt water used for the direct refrigeration of fresh products displayed on a stall.

The device can comprise a means of heating able to evaporate the residual liquid in said device after it is stopped. The same means of heating can be used to heat the water contained in the device to a temperature that is sufficient to decrease its content in pathogenic germs.

The device according to the invention can also comprise at least one means for detecting the lack of liquid combined with a feedback loop in order to cut off or decrease the intensity of the acoustic waves emitted by the piezoelectric component in the event of a lack of water. This means of detection can be a sensor (for example a sensor of the level of water in the primary reservoir, and/or a sensor of the pressure in the pressurizing chamber), or a plurality of sensors, and/or can include a measurement of an electrical parameter of the circulation pump.

Another object of the invention is a method for starting a device according to the invention, wherein:

(a) liquid is made to enter the primary reservoir via the inlet opening;

(b) when the level of said liquid rises in said primary reservoir to a pre-set point which is detected by a water level detector in the primary reservoir, the circulation pump is put into operation;

(c) the circulation pump creates a liquid pressure sufficient so that the liquid can invade the nozzle, optionally after having invaded the pressurizing chamber, and in order to form a stable liquid jet that emerges from the outlet opening, knowing that during at least a portion of this time, liquid is made to enter the primary reservoir via the inlet opening;

(d) when the level of said liquid in said primary reservoir has reached a pre-set point which is detected by a level detector, the electrical power supply of the piezoelectric component is activated in order to create droplets of liquid.

More particularly, said method for starting can be applied to a nebulizer device that is able to generate and diffuse a mist of micro-droplets in order to freshen and/or humidify the ambient atmosphere of a premises and/or in order to freshen and/or humidify products exhibited on a sales display case, and/or to freshen and/or perfume the atmosphere of a passenger compartment, said device comprising:

- a nebulizer nozzle provided with at least one opening for the intake of liquid and with at least one liquid-outlet opening, and on the side opposite said outlet opening a piezoelectric component which can emit acoustic waves into the liquid, and the transversal section of said nozzle having a progressive narrowing in the direction of said first outlet opening, in such a way that in said nozzle the acoustic waves are focused in order to create a mist of droplets of said liquid (knowing that in said nozzle the acoustic waves are able to be focused for example on said outlet opening);
- a collection reservoir which supplies said nozzle with liquid,
- a pump referred to as "circulation pump" connected on the one hand to the collection reservoir and on the other hand to said nozzle by the at least one intake opening provided in said nozzle, said circulation pump being able to generate in said nozzle a liquid pressure sufficient to maintain a liquid jet emerging via said outlet opening of the nozzle,
- a pressurizing chamber through which passes the liquid emerging from the circulation pump before entering said nozzle, said nebulizer device being characterized in that the volume of the upper part of the pressurizing chamber at a liquid level which is higher than the highest of the following three points: the opening for the intake of water of the highest nozzle, the upper edge of the outlet opening of the nozzle, the highest point of the ceramic component, is at least twice (preferably at least six or even more preferably at least twelve times) as large as the volume of the nozzle.

This device to which is applied said method of starting can have all of the alternatives described in relation with this device, or only some of them.

In the step (d) of said method for starting, said pre-set point and/or said level detector can be the same as in step (b).

Another object of the invention is the use of the nebulizer device according to the invention to generate and diffuse a mist of micro-droplets in order to freshen and/or humidify the ambient atmosphere of a premises and/or in order to freshen and/or humidify products exhibited on a sales display case, and/or to freshen and/or perfume the atmosphere of a passenger compartment of a vehicle, in particular of a land, sea or air vehicle.

DRAWINGS

The device according to the invention is shown diagrammatically in FIGS. 1 to 5 which show various embodiments of it.

Figure 1B:
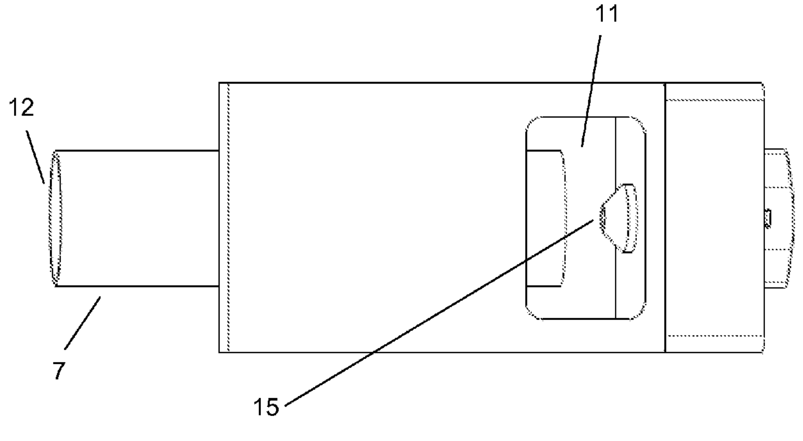

FIGS. 1*a* and 1*b* show a device according to the invention, as a side view (FIG. 1*a*) and seen from the top (FIG. 1*b*).

FIGS. 2*a* to 2*d* diagrammatically and successively show four phases of the starting and of the operation of the device of FIGS. 1*a* and 1*b*.

Figure 3A:
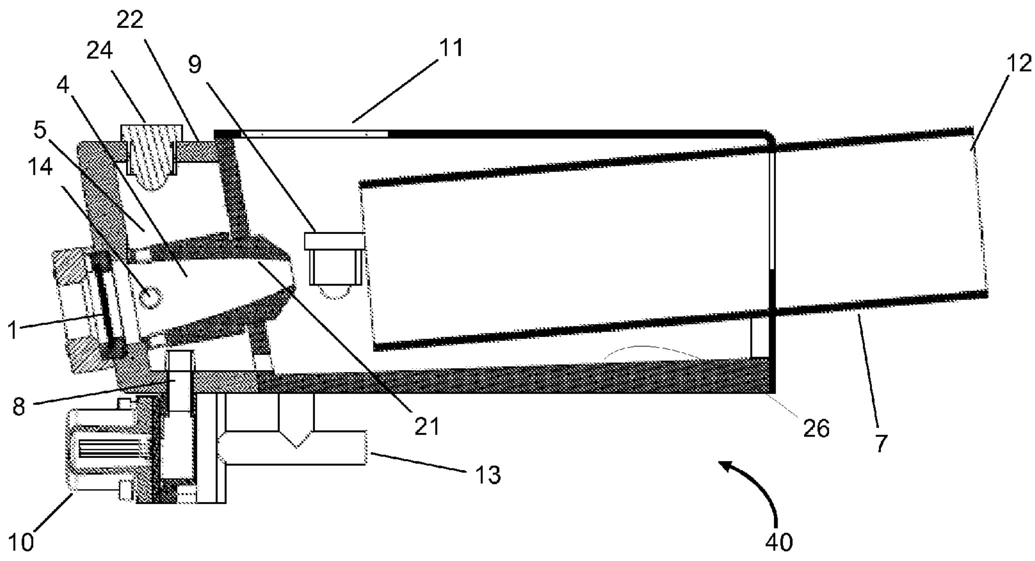
Figure 3B:
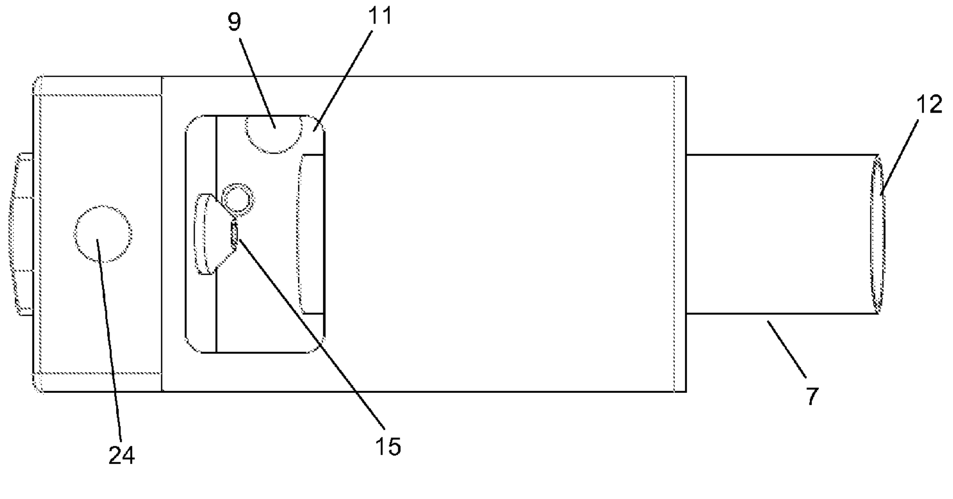

FIGS. 3*a* and 3*b* show another device according to the invention, as a side view (FIG. 3*a*) and seen from the top (FIG. 3*b*).

FIGS. 4*a* to 4*d* diagrammatically and successively show four phases of the starting and of the operation of the device of FIG. 3.

Figure 5A:
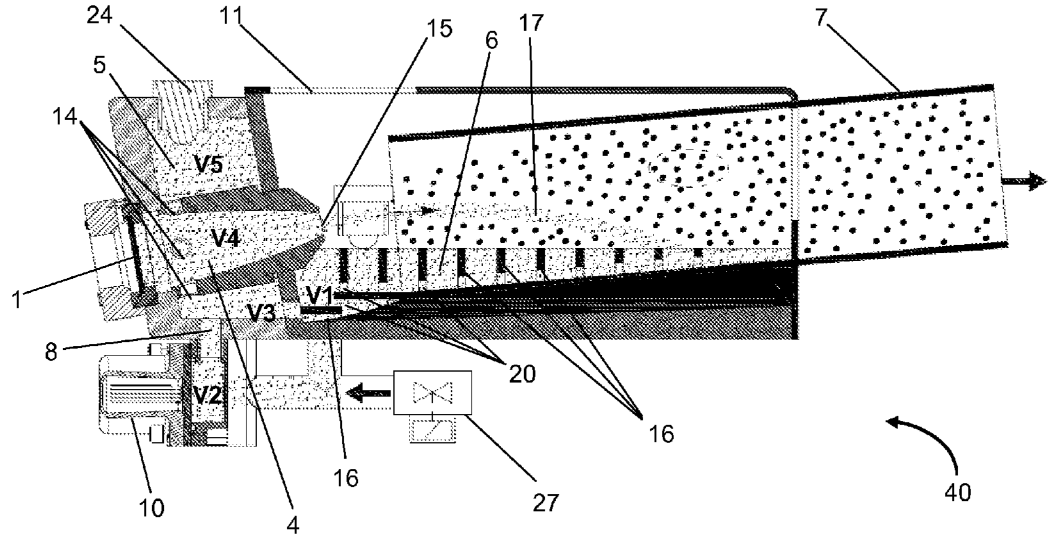
Figure 5B:
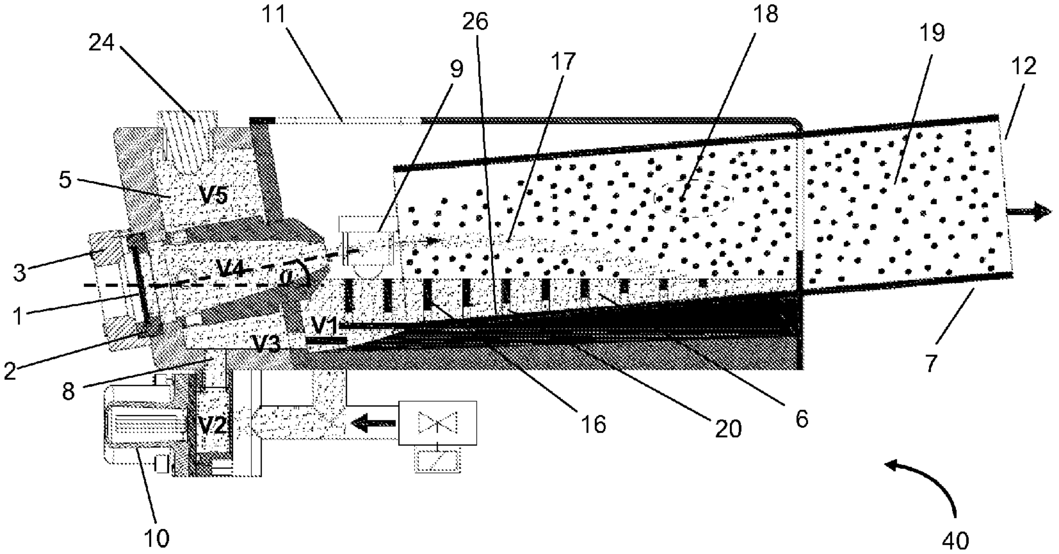

FIGS. 5*a* and 5*b* show another embodiment of the device according to the invention, FIGS. 5*a* and 5*b* showing the same device and can be distinguished solely by the numerical marks and geometrical marks that were not all able to be placed on the same Figure due to encumbrance.

DESCRIPTION

The nebulizer system or device 40 according to the invention comprises a concentration nozzle 4, of a known type, able to contain a liquid to be sprayed (typically water) and having an outlet opening 15, the transversal section of the inside of said concentration nozzle 4 having a progressive narrowing in the direction of said outlet opening 15. Said nozzle 4 further has, on the side opposite its outlet opening 15, a (ceramic) piezoelectric component 1 which can emit acoustic waves into the liquid. The inner wall of said nozzle 4 is made from a hard material that can reflect the acoustic waves generated by said piezoelectric component 1. The converging shape of the inner walls of the nozzle 4 is determined in such a way as to focus the ultrasound acoustic waves at a location close to the central portion of the outlet opening 15; as such is generated a mist of micro-droplets of the liquid to be sprayed when the nozzle 4 is filled with liquid and the ceramic component 1 emits acoustic waves of suitable frequency and intensity. Said converging shape of the inner walls of the nozzle 4 is more preferably parabolic, which improves the output of the concentration nozzle 4. Said shape of the inner walls of the tank 4 shows very advantageously a radial symmetry.

According to the invention, and as shown in FIG. 1, the longitudinal axis of the nozzle 4 is inclined in relation to the vertical. This inclination, expressed by the angle $\alpha$ with respect to the horizontal (see FIG. 5*b*), aims to decrease the total height of the device 40. The angle $\alpha$ can be less than 65°, more preferably less than 45°, more preferably less than 30° and further more preferably less than 15°. It can be 5° or 0° (longitudinal axis of the nozzle oriented in the horizontal plane), and can even be negative, because during the operation of the piezoelectric component 1, the inside of the nozzle 4 is filled with the liquid to be sprayed by a pump 10 which maintains a liquid pressure in said nozzle 4; this requires a pump 10 with a sufficient capacity. The inclination can be −90°, i.e. that the outlet opening 15 is located at the bottom of the nozzle 4; this provides a good output of mist but the nebulizer system 40 then has a greater height than when the inclination $\alpha$ is 0°; this greater height can make it more difficult to integrate into a vehicle passenger compartment.

The inventors found that an angle $\alpha$ between 0° and 45° (preferably between 0° and 30°, and even more preferably between 5° and 20°) provides an excellent compromise between the nebulizer performance, the size of the pump 10 and the encumbrance of system 40 (to which contributes the dimension of the pump 10). In the framework of this invention an angle $\alpha$ between 0 and 30° is preferred, and preferably between 5 and 20°.

In a known manner, the nozzle 4 comprises at least one opening for the intake of liquid 14 making it possible to fill said nozzle 4 with the liquid to be sprayed. This filling has two functions. On the one hand, knowing that in operation, a portion of the liquid contained in the nozzle 4 exits in the form of mist, it is necessary to supply the nozzle 4 again with liquid. On the other hand, a continuous filling of the nozzle 4 combined with the recirculation of the liquid makes it possible to stabilize the operating conditions of the system 40 even in the presence of strong accelerations of the system, as can be found in a land, sea or air vehicle for example.

For this purpose, said nozzle 4 is supplied with liquid by at least one reservoir of liquid 6, referred to as "primary reservoir" or "collection reservoir". A pump 10 referred to as "circulation pump" connected on the one hand to said primary reservoir of liquid 6 and on the other hand to the nozzle 4 (by the intermediary of a conduit 8) makes it possible to constantly circulate the liquid in the nozzle 4 and to generate a liquid jet 17 at the outlet of the outlet opening 15 of the nozzle 4. Said circulation pump 10 is advantageously located directly above the collection reservoir 6, as can be seen in the Figures, in order to prevent as much as possible its loss of prime due to a lack of water.

The intake of the liquid coming from the primary reservoir of liquid 6 in the nozzle 4 is done through at least one intake opening 14. Preferably, a plurality of intake openings 14 are arranged around the longitudinal axis of the nozzle 4 in a zone close to the ceramic piezoelectric component 1.

The nebulizer system 40 according to the invention comprises a pressurizing chamber 5 which communicates with the nozzle 4 by at least one opening 14 for the intake of water in the nozzle. According to the invention, this pressurizing chamber 5 has a certain interior volume with respect to the volume of the nozzle 4, which provides for a better stability of the water pressure in the nozzle 4 in disturbed conditions as described hereinabove; this will be explained hereinbelow in a detailed manner in relation with FIG. 5.

According to the invention, this pressurizing chamber 5 can have different shapes. In an alternative shown in FIG. 1, the nozzle 4 is carried out with a double wall, with the inner wall 21 being the wall properly speaking of the nozzle 4, that can reflect the acoustic waves, as described hereinabove, and the outer wall 22 enclosing with the wall 21 of the nozzle 4 a volume that forms said pressurizing chamber 5. The pressurizing chamber 5 enclosed between its outer wall 22 and the wall 21 of the nozzle 4 is connected, on the one hand, to the inside of the nozzle 4 by at least one opening for the intake 14 of liquid (and preferably, as indicated hereinabove, by a plurality of intake openings 14 arranged radially, for example four openings), and on the other hand to the collection reservoir 6 by the intermediary of the conduit 8.

In the embodiment of the invention shown in FIG. 1, the collection reservoir 6 and the nozzle 4 form a single-block element. This makes it possible to simplify its construction; such a single-block element is more robust and resists the disturbed environment of a vehicle better.

The outlet opening 15 of the nozzle 4 more preferably has a circular shape. In an embodiment, its diameter is between 3 and 8 mm, and advantageously between 4 and 6 mm; the inside length of the nozzle is between 25 mm and 42 mm, knowing that this distance corresponds to the near-field ultrasound generated by the ceramic piezoelectric component 1. By way of example, a nozzle with a height of 38 mm can be used, with an outlet opening of a diameter of 6 mm. The intake section of the nozzle 4 (i.e. the sum of the surfaces of the intake openings 14) must be greater than the section of the outlet opening 15 (more preferably at least three times higher) in order to prevent the phenomenon of cavitation in the nozzle 4 (as well as a lack of water). This condition is satisfied for example with four intake openings 14 of a diameter of 5 mm for an outlet opening 15 of a diameter of 6 mm.

In particular for the use of the nebulizer system 40 in a vehicle, it is advantageously provided that the liquid jet 17 generated at the output 15 of the nozzle 4 empties into a collection tube 7 of which the longitudinal axis is more preferably inclined in relation to the vertical. The collection tube 7 can be passed through by a flow of air generated by a means of ventilation (not shown in the Figures), which is more preferably able to be adjusted for the flow and which is located upstream, downstream or inside the collection tube 7. Said flow of air enters into the nebulizer system 40 by an air inlet 11 and carries off the micro-droplets of water 18 generated by the nozzle 4 around the water jet 17. A mist 19 of micro-droplets is as such formed which exits the collection tube 7 via its outlet 12 and enters into its destination environment, for example the passenger compartment of a vehicle. The water jet 17 is projected against the inner wall of the collection tube 7, and the liquid collected as such is placed in the water tray 6. As such the collection tube 7 is also used as a tube for guiding the diffusion of the mist. This embodiment can also be suitable for a stationary nebulizer system 40, in particular a system mounted on a stall.

In an embodiment of the invention, the device comprises, in addition to the primary collection reservoir 6, a reservoir of liquid referred to as secondary (not shown in the Figures), which can be offset and connected to the circuit of liquid represented by the primary collection reservoir 6 and the nozzle 4 by a conduit. This makes it possible to reduce the size and the encumbrance of the primary reservoir 6. Said secondary reservoir of liquid can be made from any suitable material, which can be flexible, rigid or semi-rigid. It can in particular be made of metal (in particular aluminum, stainless steel) or of plastic (in particular PE and PP). As will be explained in greater detail hereinbelow, the secondary reservoir can comprise or contain a heating resistance or more generally a means of heating, in order to provide for the hygiene, in particular bacteriological, of this volume of water by heating the water and/or the walls to a temperature that is sufficient to destroy at least partially pathogenic germs, and more generally to disinfect and/or dry the entire device 40.

Generally, the ceramic piezoelectric component 1 is more preferably of cylindrical shape, typically a circular-shaped plate. By way of example, it can have a diameter of 20 mm or 25 mm. The ultrasound frequency is advantageously between 1.3 kHz and 2.3 kHz. It can be for example 1.68 MHz.

In an embodiment, the ceramic piezoelectric component 1 is fixed on the outer wall 22 of the pressurizing chamber 5 to the base 23 of the nozzle 4 by a support 3; a seal 2 provides the seal between said pressurizing chamber 5 and the support 3.

Said piezoelectric component 1 can absorb a substantial electrical power, for example 40 W for a diameter of 20 mm. Approximately 40% of this power is output in the form of acoustic energy transmitted to the liquid, the remainder is dissipated in thermal form. For this reason, during its operation, the piezoelectric component 1 must be cooled constantly by the liquid in order to prevent it from deteriorating from overheating. The inventors realized that when the piezoelectric component 1 operates dry even for a very short period, it risks becoming damaged or even destroyed. In order to prevent this, the inventors have provided that the nebulizer system 40 comprise suitable means that are able to prevent said piezoelectric component 1 from operating (i.e. does not emit acoustic waves or only acoustic waves of very low power) when the piezoelectric component 1 is not immersed in the liquid to be sprayed. These means can have different forms, and include in general at least one means for detecting the lack of liquid and/or a means for detecting the heating of the piezoelectric component 1, and a means of feedback on the electrical power supply of said piezoelectric component Said means for detecting the lack of liquid can be a level sensor 9 or a presence sensor which cuts off or adjusts the operation of the piezoelectric component 1. This sensor 9 can be an optical sensor or a capacitive sensor or an inductive sensor, but among these three, an optical sensor is preferred which has better reliability. This sensor 9 can be located at different locations, in particular in the collection container, or in the inside of the nozzle 4, or in the pressurizing chamber 5 of the nozzle 4. In an embodiment a sensor located in the primary reservoir 6 is used. An ultrasound sensor can also be used, acting as an analog sensor making it possible to measure the instantaneous flow rate of the system.

Said means for detecting the lack of liquid can be a sensor that detects the presence of the liquid jet 17 at the outlet of the outlet opening 15 of the nozzle 4. This means is preferred less as it results in a delay in detecting an immersion defect of said piezoelectric component 1.

Said means for detecting the lack of liquid can be a sensor of the pressure in the nozzle 4 and/or in the pressurizing chamber 5 and/or at the outlet of the circulation pump 10 and/or in the conduit 8.

Another means for detecting the lack of liquid in the nozzle 4 is a detector of the temperature at the surface and/or inside said piezoelectric component 1, which makes it possible to detect the quick heating of said piezoelectric component 1 before any damage occurs. This detection can take place for example using a thermocouple. In the framework of this invention the heat detection on the piezoelectric component 1 is not however a preferred embodiment: means are preferred that detect the lack of liquid more directly, and at an earlier stage at which the lack of liquid has not yet disturbed the operation of said piezoelectric component 1.

Two or several means for detecting can be combined, selected from among those that have just been presented and/or from among those that will be presented hereinbelow.

Various types of pumps can be used for the circulation pump 10. It must have a flow that can be adjusted; a pump that can be adjusted between 0.1 and 2.8 liters/min is suitable for a nozzle 4 that has the dimensions indicated hereinabove. In an advantageous embodiment, which is suitable in a miniaturized system that can be used for the passenger compartment of a vehicle, the circulation pump 10 can be a propeller pump. Advantageously, this pump absorbs a direct current and the voltage is adjusted in order to vary the rotation speed and therefore the discharge pressure at the outlet of the nozzle 4, which makes it possible to modify the length of the jet 17.

Generally, a system such as described hereinabove has the risk that the circulation pump 10 temporarily sucks air rather than liquid when the level of water in the collection reservoir 6 changes substantially, for example following a sudden acceleration, braking or tipping of the vehicle. There is also the risk of air bubbles forming in the collection reservoir 6 if the environment is highly disturbed; these air bubbles can be swallowed by the pump 10. The sucking of air can even lead to a temporary or permanent loss of prime of the pump. This risks leading to a drop in the water pressure in the nozzle 4 and to a lack of liquid such that the piezoelectric component 1 is no longer immersed.

In order to prevent a lack of liquid in the nozzle 4, three means are proposed that can be combined (and to which may be added where applicable means for detecting the lack of liquid presented hereinabove): The collection reservoir 6 can have a shape characterized by a bottom 26 at least partially inclined of which the low point is close to its discharge opening 25; this shape can be a funnel shape as in FIG. 1 or another shape as in FIGS. 3*a* and 5. Moreover, as shown in the FIGS. 1, 2 and 5, the collection reservoir 6 can be compartmentalized by at least one plate 16 referred to as "stabilization plate" which has for effect to stabilize the level of liquid, and preferably a plurality of such stabilization plates, that can be arranged in the vertical, horizontal or inclined direction. Said stabilization plate 16 is a plate comprising at least one opening 20 through which the liquid can flow. The third means announced hereinabove is linked to the volume of the pressurizing chamber 5; it will be presented hereinbelow in relation with FIG. 5.

As indicated hereinabove, the collection reservoir 6 can comprise at least one stabilization plate 16 for the level of liquid which is substantially horizontal which extends over all or a portion of the width of the reservoir, and it can, also or in addition, comprise at least one plate which is not horizontal, for example a vertical plate, which extends over all or a portion of the height of said reservoir. The reservoir can comprise plates which are substantially parallel. Preferably, the openings 20 of two adjacent parallel plates 16 are not located in the same place, i.e. are not superposed, but are offset in the plane of the plate.

FIG. 1 shows an example of a collection reservoir 6 in the shape of a funnel provided with three horizontal and parallel plates 16 for stabilizing the level of the liquid; their openings 20 are not superposed. The collection reservoir 6 can comprise a discharge of the liquid (not shown in the Figures) in its lower portion which advantageously constitutes the lowest point of the nebulizer system; as such, the dead volume is minimized in the event of a stoppage of the system 40, after being emptied via this lowest point.

In order to further improve the effect of the stabilization plates 16, at least one portion of said openings 20 can be closed off at least partially by a valve which opens at least partially under a water pressure coming from one side and closes under a water pressure coming from the other side, or opens not as widely under a water pressure coming from one side as under an equivalent water pressure coming from the other side.

In an alternative which can be combined with the valves, said stabilization plates 16 can be carried out entirely or partially in the form of grilles or strainers.

Figure 4A:
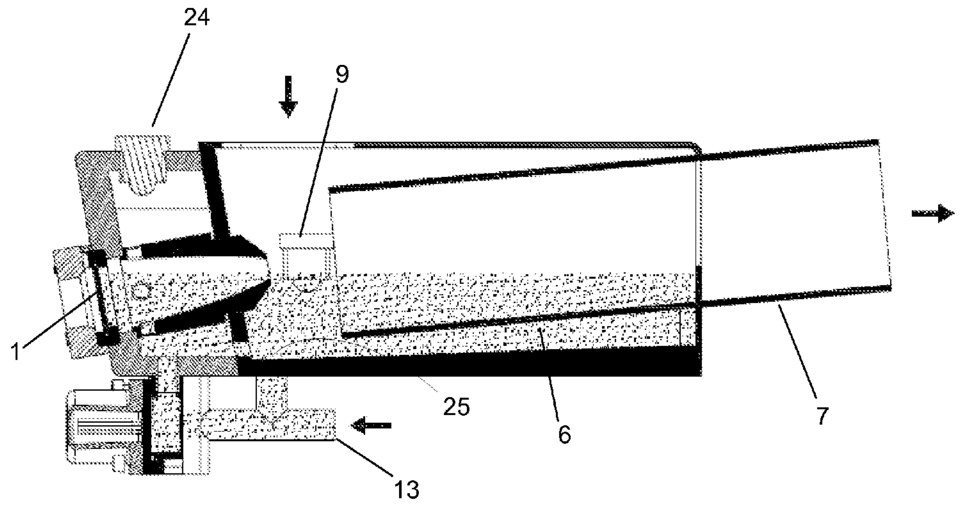
Figure 4B:
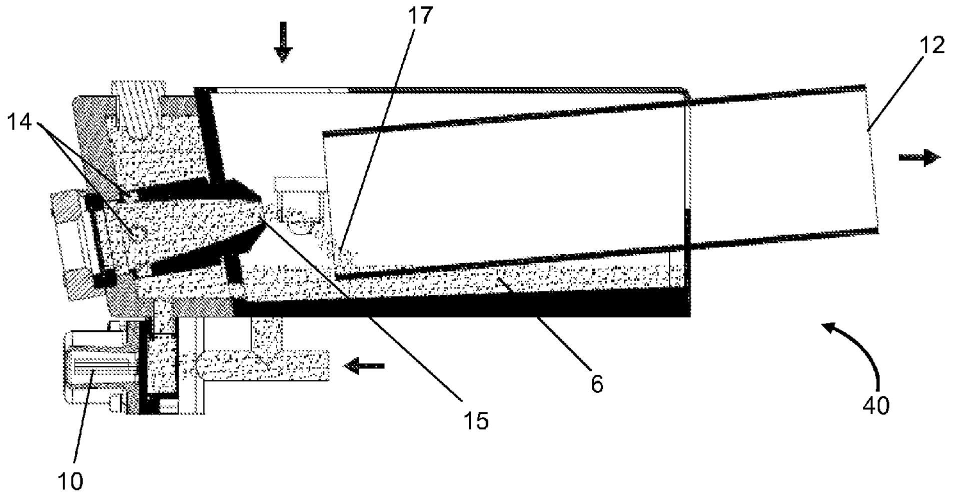
Figure 4C:
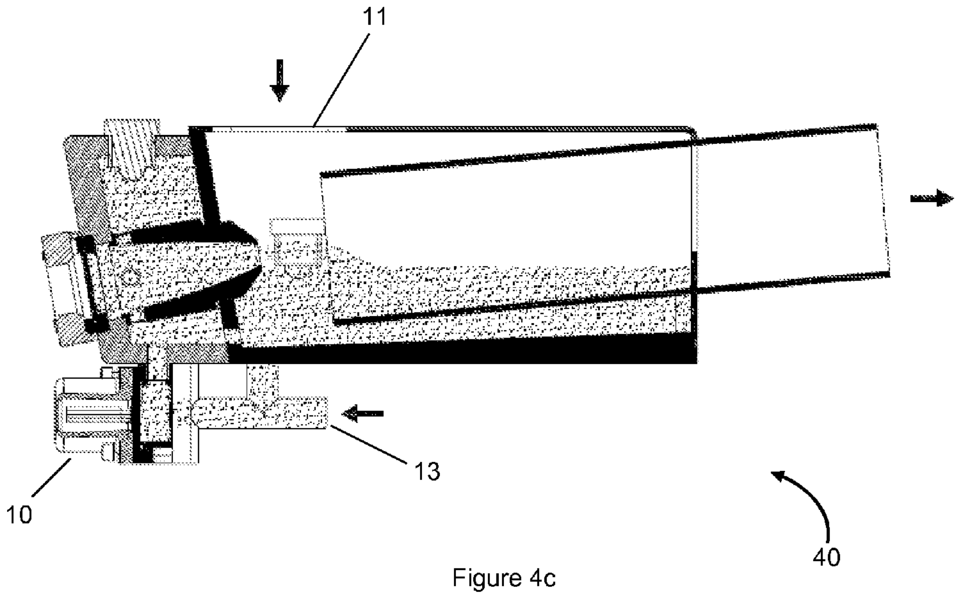
Figure 4D:
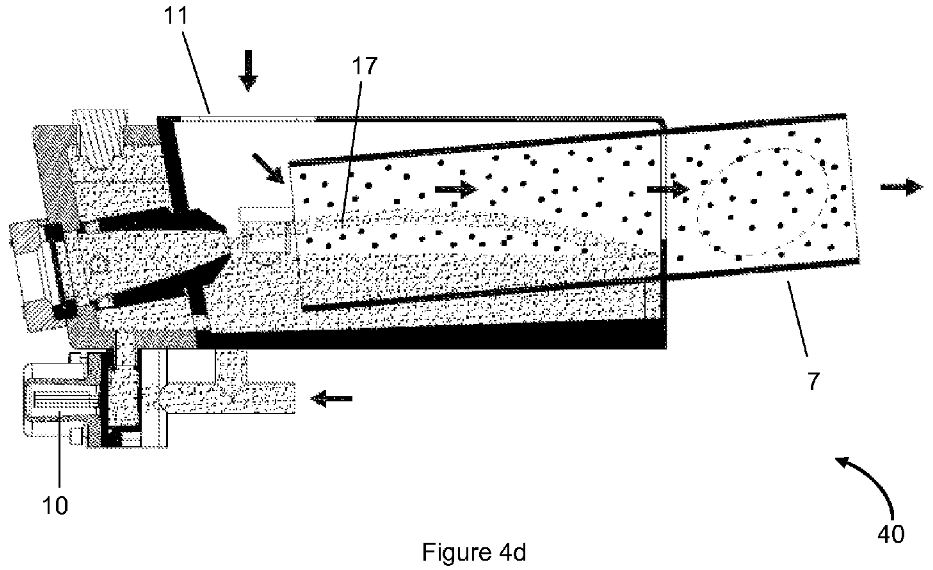

At least one stabilization plate 16 can also be positioned in the guiding tube 7 such as is diagrammatically shown in FIG. 4*d*. This solves a problem which is proper to nebulizer systems of which the nozzle 4 has a longitudinal axis that is inclined in relation to the vertical and of which the liquid jet 17 is collected in a guiding tube 7: there is a risk of air bubbles forming during the collection of the liquid of the jet; these bubbles can be found in the collection reservoir 6 and be sucked by the circulation pump 10, of which they are able to disturb the proper operation. The inventors have found that a stabilization plate 16 arranged in the guiding tube 7 can reduce the formation and the transport of air bubbles.

Figure 2A:
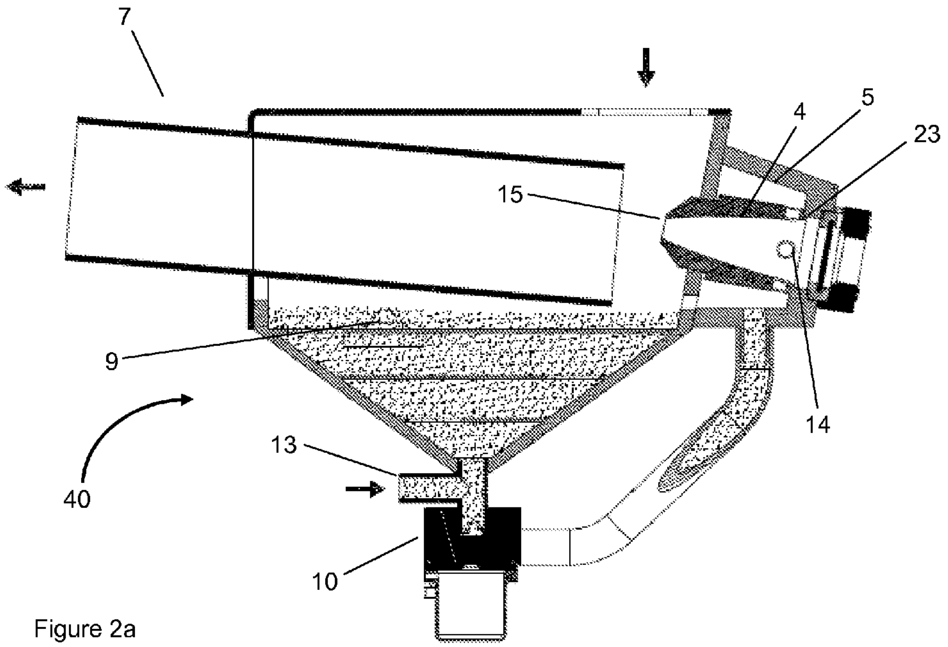

FIGS. 2*a* to 2*d* diagrammatically and successively show the starting and the operation of the device 40 according to the invention shown in FIG. 1. As shown in FIG. 2*a*, the system 40 is filled by having liquid enter through the inlet opening 13. The filling can be carried out through a solenoid valve or through a peristaltic pump or other types of pump (piston, membrane, etc.) (not shown in Figure) located upstream of the inlet 13; this filling causes the level of liquid to rise in the reservoir 6 and the conduit 8 until a point detected by a water presence sensor 9 starting from which the circulation pump 10 is started.

Figure 2B:
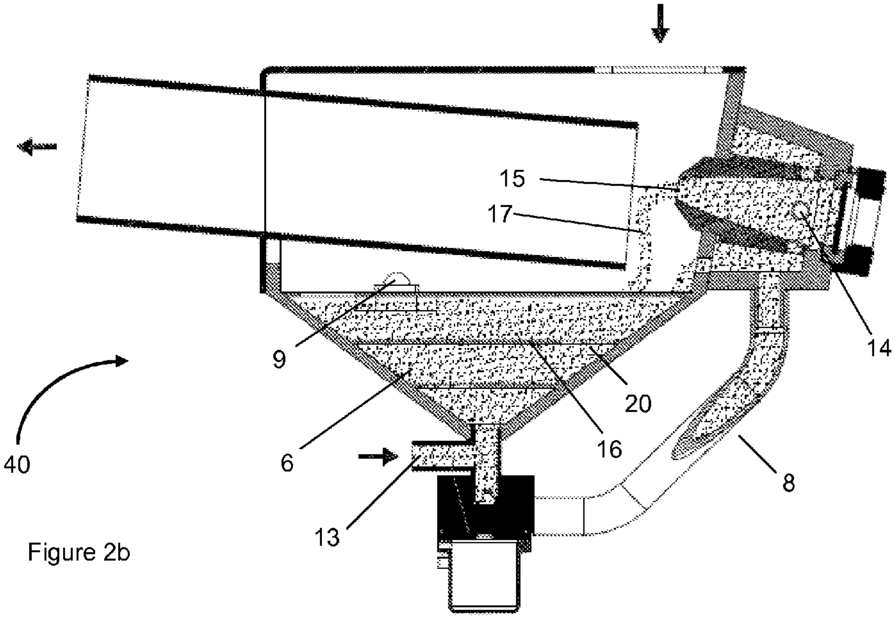

As shown in FIG. 2*b*, the progressive filling of the reservoir 6 via the inlet opening 13 and the pressure generated by the circulation pump 10 cause the liquid to invade the pressurizing chamber 5 then the nozzle 4, and a short water jet 17 exits from the outlet opening 15.

Figure 2C:
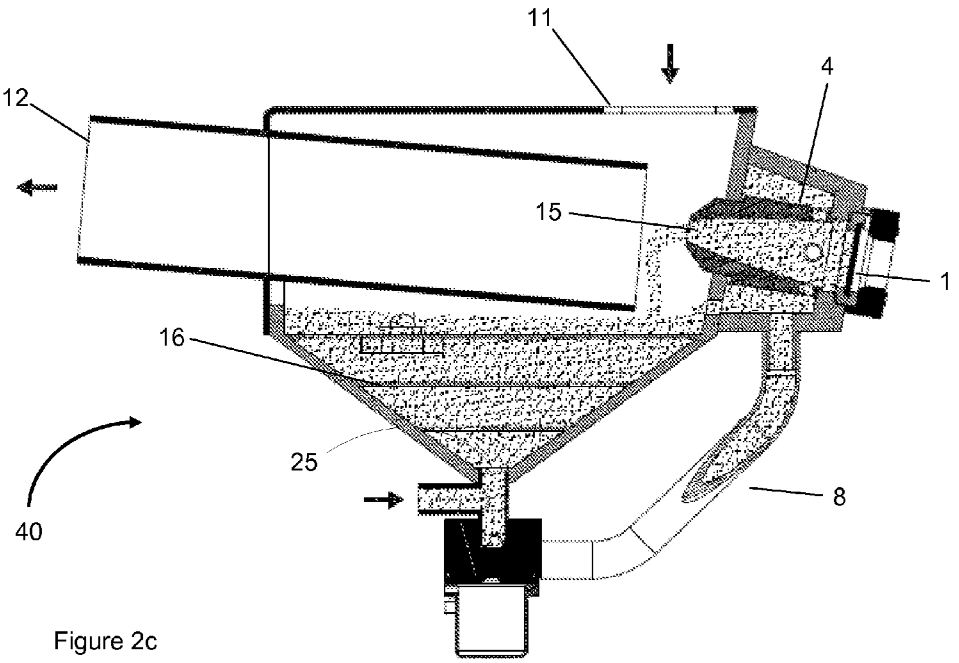
Figure 2D:
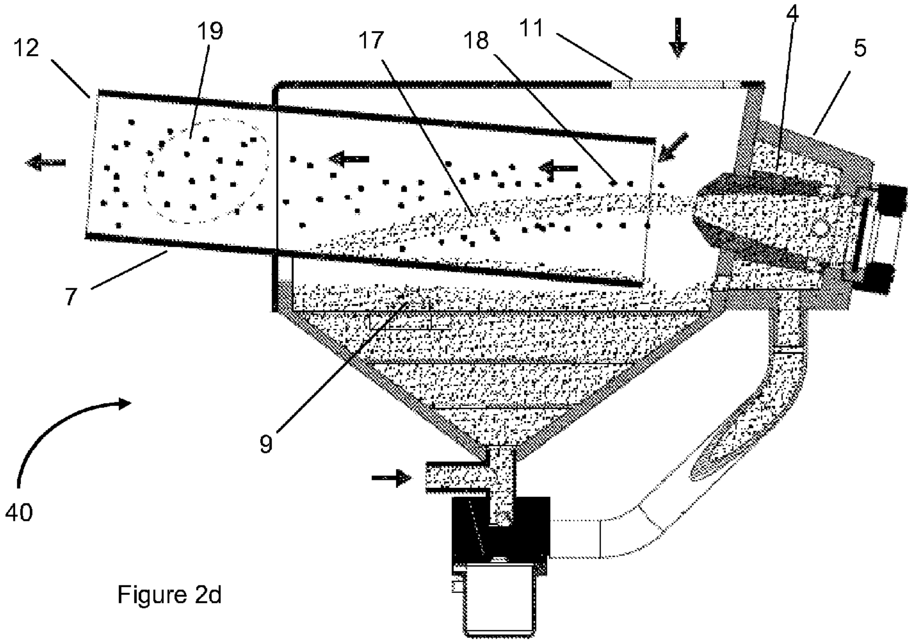

When the level of liquid in the reservoir 6 is again sufficient (such as detected for example by the water presence sensor 9) and the piezoelectric component is fully immersed, see FIG. 2*c*, the electrical power supply of the piezoelectric component 1 is activated. The ceramic component 1 is excited at its resonance frequency, which has for consequence to generate an acoustic wave which is channeled by the nozzle 4 acting, thanks to the specific shape of its inner wall, as a concentrator of acoustic waves. As shown in FIG. 2*d*, the water jet 17 is extended under the effect of the acoustic waves until it flows into the guiding tube 7, and micro-droplets 18 of water are pulled off by the acoustic wave. Under the effect of the flow of air (represented by the arrows), a mist 19 is formed it exists the guiding tube 7 via its nebulization outlet 12. The water jet 17 is collected by the guiding tube 7 and the water is collected in the collection container 6 in order to be recycled in the system 40.

When the level of water such as detected by the water presence sensor 9 is insufficient to ensure that the piezoelectric component 1 is entirely immersed, a feedback loop interrupts or reduces the operation of the piezoelectric component 1. If this drop in the level is prolonged beyond a certain period of time, water is added by the filling inlet 13, if possible, for example from said secondary reservoir. The adding of water can also be done permanently, continuously or discontinuously, for example using a peristaltic pump (not shown in the Figures), in order to offset the loss of water due to the nebulization.

FIG. 3 shows another embodiment of the invention that is distinguished from that of FIG. 1 by the shape of the primary collection reservoir 6 and by the shape of the pressurizing chamber 5 (which will be explained in further detail in relation with FIG. 5). The nebulizer device 40 according to FIG. 3 is provided with a second sensor 24 of the presence of water which is located in the pressurizing chamber 5, more preferably in the upper portion of the latter; this second sensor 24 is optional.

More precisely, the primary collection reservoir has a shape characterized by a bottom at least partially inclined of which the low point is close to its discharge opening 25, but this shape is not that of a funnel as in FIG. 1. The device according to FIG. 3 does not show any stabilization plates 16, but the latter can be added (for example in a manner similar to that which is shown in FIG. 5*b*).

FIGS. 4*a* to 4*d* diagrammatically and successively show the starting and the operation of the device 40 according to the invention shown in FIG. 3; this method is similar to that explained hereinabove in relation with FIGS. 2*a* to 2*d*. As shown in FIG. 4*a*, the system 40 is filled by causing liquid to enter through the inlet opening 13. As in the case of FIG. 2*a*, the filling can be done through a solenoid valve or through a peristaltic pump or other types of pump (piston, membrane, etc.) (not shown in Figure) located upstream of the inlet 13; this filling causes the level of liquid to rise in the reservoir 6 and the conduit 8 until a point detected by a water presence sensor 9 starting from which the circulation pump 10 is started.

As shown in FIG. 4*b*, the progressive filling of the 6 par the inlet opening 13 and the pressure generated by the circulation pump 10 cause the liquid to invade the pressurizing chamber 5 then the nozzle 4, and a short water jet 17 exits from the outlet opening 15.

When the level of liquid in the reservoir 6 is again sufficient (such as detected for example by the water presence sensor 9) and the piezoelectric component is fully immersed, see FIG. 4*c*, the electrical power supply of the piezoelectric component 1 is activated. The ceramic component 1 is excited at its resonance frequency, which has for consequence to generate an acoustic wave which is channeled by the nozzle 4 acting, thanks to the specific shape of its inner wall, as a concentrator of acoustic waves. As shown in FIG. 4*d*, the water jet 17 is extended under the effect of the acoustic waves until it flows into the guiding tube 7, and micro-droplets 18 of water are pulled off by the acoustic wave. Under the effect of the flow of air (represented by the arrows), a mist 19 is formed it exists the guiding tube 7 via its nebulization outlet 12. The water jet 17 is collected by the guiding tube 7 and the water is collected in the collection container 6 in order to be recycled in the system 40.

When the level of water such as detected by the water presence sensor 9 is insufficient to ensure that the piezoelectric component 1 is entirely immersed, a feedback loop interrupts or reduces the operation of the piezoelectric component 1. If this drop in the level is prolonged beyond a certain period of time, water is added by the filling inlet 13, if possible, for example from said secondary reservoir. The adding of water can also be done permanently, continuously or discontinuously, for example using a peristaltic pump (not shown in the Figures), in order to offset the loss of water due to the nebulization.

In all of the embodiments, a second water presence sensor 24 can be provided at the top of the pressurizing chamber 5: if this sensor indicates an insufficient level of liquid, a feedback loop can cut off or decrease the supplying of the piezoelectric component 1 and/or increase the flow rate of the circulation pump 10. As such, the volume of the chamber makes it possible to provide a protection for the piezoelectric component 1, during the time that its supply is cut off and the piezoelectric component 1 ceases to resonate.

FIG. 5 shows another embodiment of the invention. The guiding tube 7 here forms at least partially the collection reservoir 6, in such a way that its inclined bottom forms at least partially the inclined bottom of said collection reservoir 6. It comprises at least one stabilization plate 16, and preferably (as in FIG. 5) a plurality of stabilization plates 16, arranged for example horizontally and/or vertically. This embodiment allows for a particularly compact construction of the nebulizer system 40 and of which the tolerance to mechanical disturbances is excellent. It is not a problem if in the event of a substantial mechanical disturbance (impact) the level of liquid of the collection reservoir 6 occasionally and temporarily overflows over the level of the outlet opening 14 of the nozzle 4, in such a way as to drown the water jet 17: this momentarily interrupts the production of mist 19, but does not place the ceramic component in danger, and will not result in an effect that can be perceived for the user of the system.

FIG. 5 shows an essential aspect of the invention which is explained here in detail. It is linked to the relations between different volumes. V1 designates the volume of liquid in the collection reservoir 6, V2 the volume of liquid in the circulation pump 10, V3 the volume of liquid in the pressurizing chamber 5 in the lower portion of the nozzle 4 (i.e. less than the height that defines the lower plane of the volume V5, see hereinbelow) and V4 the volume of liquid in the nozzle 4. The volume V3 can be very low and even zero.

V5 designates the volume of liquid in the upper portion of the pressurizing chamber 5 at a liquid level which is higher than the highest of the following three points: the opening 14 for the intake of water of the highest nozzle, or the upper edge of the outlet opening 15 of the nozzle 4, the highest point of the ceramic piezoelectric component 1. As such regardless of the inclination a of the nozzle 4, every point of the ceramic piezoelectric component 1 is located at a level less than the volume V5.

In normal operation of the system 40 (see for example FIGS. 2*d* and 4*d*), the volumes V1, V2, V3, V4 and V5 are filled with liquid, the circulation pump 10 and the piezoelectric component 1 are operating and are generating a water jet 17 of a length that is approximately constant, which illustrates the stationary state of the system.

According to the invention, the pressurizing chamber 5 is sized in such a way that it has a buffer volume (safety volume) V5 that is sufficient with respect to the volume V4 of the nozzle 4, in such a way that in the case where the circulation pump 10 is no longer pumping liquid (for example when the level of liquid in the collection reservoir 6 is insufficient, or when the circulation pump 10 has lost its prime), the volume V5 ensures during a certain lapse of time ts the supplying with water of the volume V4 of the nozzle 4, in such a way that the piezoelectric component 1 is still immersed during this lapse of time ts. This lapse of time ts can be, all or in part, used to cut off the supply of the piezoelectric component 1, and/or to wait if the level of liquid is reestablished on its own (in particular in the case of a mechanical disturbance or when the circulation pump 10 has simply swallowed an air bubble). The time ts has to be long enough in order to allow for the complete cut-off of the supply of the piezoelectric component 1 and the stopping of its operation; the applicant has indeed observed that the stopping of the operation of the piezoelectric component 1 is not instantaneous when its electrical power supply is cut off: the piezoelectric component 1 continues to vibrate while the circuits of its electrical power supply discharge.

Generally, it is preferred in the framework of this invention that the ration of the volumes V5/V4 be at least 2 and preferably at least 6, and further more preferably at least 12.

More precisely, the desired reaction time of the system to cut off the electrical power supply of the piezoelectric component 1 in the event of a lack of water is taken into consideration. It is not necessarily desirable to cut off the supply at the slightest drop in the level in the pressurizing chamber 5, which would risk resulting in a generation of mist that is excessively intermittent. But it must be assured that when this drop is prolonged or worsens beyond a certain period of time, the electrical power supply of the piezoelectric component 1 is cut off or at least substantially reduced. As such, the inventors consider than in an unstable mechanical environment (vehicle, stall surrounded by a crowd of persons) the nebulizer system 40 according to the invention must allow for an operation of the piezoelectric component 1 for a period ts between 1 and 10 seconds without the supply of liquid by the circulation pump 10, and preferably between 2 and 5 seconds.

In this context, an important parameter is the flow of liquid generated by the piezoelectric component 1 at the outlet of the opening 14 of the nozzle 4 in the absence of pumping by the circulation pump 10; this flow (which often manifests itself by the presence of a small water jet called "acoustic fountain") depends (for a given angle α of positioning of the nozzle 4 and liquid) substantially on the power of the piezoelectric component 1.

More precisely, the flow of the acoustic fountain can be expressed by $$Q\text{piezo}=K\times P\text{max}$$

where Pmax is the maximum electrical power consumed by the piezoelectric component and Qpiezo is the flow rate of the acoustic fountain at this power Qpiezo, and K is a proportionality factor. An operating safety duration of ts seconds is desired, i.e. that when the circulation pump 10 stops operating (in particular due to loss of prime), the system has a period of about ts seconds in order to cut off the supply of the piezoelectric component 1. Advantageously, the period ts is between 1 and 10 seconds, and a value between 2 and 5 seconds is preferred. According to the invention, this objective can be achieved by providing a sufficient safety buffer volume V5, which corresponds to the volume of the pressurizing chamber 5 that is located at a level of liquid higher than the upper edge of the outlet opening 15 of the nozzle 4. This volume must be higher than the volume V4 of the nozzle 4.

It is therefore desired that V5≥V4+Qpiezo X ts.

This relation can be expressed by V5≥V4+K×Pmax X ts.

In a typical example a nozzle 4 is used with a volume V4 of 0.0054 liters, and Qpiezo is 50 W for a supply voltage of 22 V with an acoustic performance of about 40%; the angle is α between 0 and 30°. In these conditions Pmax is about 1.5 liters/min, and consequently K=0.0005 I/Ws. If the target value is ts=5 seconds, V5 must be equal to at least 0.13 liters. The V5/V4 ratio is therefore 24. As indicated hereinabove, the value ts can be less than 5 seconds, which tends to decrease the V5/V4 ratio.

The V5/V4 ratio can be estimated even more precisely, which takes into account in particular the value of the angle α and the sections of the openings 14, 15. It is however observed that except in an extreme situation (in particular: angle α less than −,30°, ratio of the sections of the outlet opening 15 and of the intake openings 14 excessively low), the magnitude of the result does not change. In order to avoid complicating this description we will present in more detail a more precise estimate in the appendix hereinbelow.

Another problem of a nebulizer system 40 is its supply with liquid. In the case where it is installed in a vehicle, it is excluded to ensure the supply with water of the system by a human operator (user of the vehicle, technician etc.), like the windshield washing system of a vehicle. In the case where the nebulizer system 40 is installed on a sales stall, an external supply of water is not always available, or cannot be monopolized by a permanent connection to the nebulizer system 40; a secondary liquid reservoir can be provided in this case of a sufficient capacity that can be filled by an operator (for example every morning or once a week). Advantageously, the nebulizer system 40 according to the invention is supplied with water by a system for recovering water coming from outside of said nebulizer system.

This recovered water can enter into the nebulizer system 40 via said secondary liquid reservoir. This can be for example water from the condensation that forms on surfaces of materials in contact with the ice melt water used for the direct refrigeration of fresh products (for example fish, seafood) displayed on a stall. It can also come from an air conditioning system, and more especially water from the condensation coming from said air conditioning system. It can be taken continuously or discontinuously into the nebulizer system 40. Regardless of the origin of the recovered water, it has to be purified before entering into the nozzle 4. The purification can be carried out by heating at a sufficient temperature for a sufficient length of time (this heating can be carried out permanently or intermittently, for example by a heating resistance), and/or by a filtering element (for example a ceramic filter able to eliminate particles of a size exceeding 1 μm and preferably exceeding 0.5 μm). In order to supply the filtering element with water to be purified, a pump (for example a peristaltic pump) can be provided which generates enough pressure to overcome the loss of charge caused by the filtering element.

Another problem is the emptying of the nebulizer system 40: it is not desired that in the case of prolonged non-use, the water stagnates in the parts of the system, as this can favor the proliferation of pathogenic germs. For this, various alternatives are proposed here.

In an advantageous embodiment, the emptying of the liquid is done by an opening provided in the lower portion of the collection reservoir 6. This opening can be the same as the one through which the water arrives to fill said collection reservoir 6 (in this alternative it is therefore the opening bearing reference 13). A solenoid valve can be provided, and/or a suction and/or filling pump.

In an alternative the primary reservoir of liquid 6 is filled by a reversible pump from the secondary reservoir of liquid. In this case, it is possible to empty the primary reservoir 6 into the secondary reservoir via this same pump; the secondary reservoir can then be emptied into the air conditioning system with which is communicated via a conduit.

In another embodiment, which is in particular suitable for the use of the nebulizer system 40 on a stall in a point of sale, the system has an external supply with water under pressure. In light of the fact that it is generally easier to install an arrival of water under pressure than a drain for water, it would be desirable to not imperatively have need for a water drain for such a nebulizer system. According to the invention, the nebulizer system 40 comprises means for heating which allow it to be emptied via full evaporation of the liquid. The water vapor generated as such can also be used to decontaminate at least partially the system (in particular the shafts and pipes for the circulation of the mist and of the tube for guiding the diffusion 7, of the volume V1 as well as volumes V2, V3, V4 and V5).

Preferably, this means of heating is a heating resistance that cannot overheat if it is used dry; a heating resistance coated with silicone of a known type can be suitable. This heating resistance can be installed inside the collection reservoir 6. It can be used in different ways. In particular, it can intermittently heat the water to a temperature that is sufficient to kill certain types of pathogenic germs, such as germs that cause Legionnaire's disease contained in the liquid of the system and on its walls. It can also be used to evaporate all of the stagnant liquid in the system during a prolonged stoppage. This avoids the use of bactericidal products. For this purpose, the temperature must be able to reach at least 70° C., as described in patent application WO 2011/039487 of the applicant.

The device 40 according to the invention, thanks to its nozzle 4 focusing acoustic waves generated by a piezoelectric component 1, is able to create and diffuse a mist formed of droplets of a typical average diameter between 0.5 μm and 10 μm, preferably between 1 μm and 5 μm. This size of particles depends in particular on the frequency of the acoustic waves produced by said piezoelectric component 1. It can be used on board any type of vehicle, in particular land, air or sea. It can be used therein in particular in order to freshen and/or humidify and/or perfume and/or disinfect the air of a passenger compartment (for example the cabin of a railway car, vessel or aircraft) or of a volume of transport of products. It can also be used in stationary applications, for example in commercial, artisanal, industrial premises or in a dwelling, in order to freshen and/or humidify and/or disinfect and/or perfume the ambient air. It can be used in particular in order to freshen and/or humidify products (in particular fresh products) displayed for sale on a stall. This device 40 has the advantages of being particularly compact (thanks to its design with inclined nozzle 4 which empties its water jet into the guiding tube 7 of the diffusion of the mist), particularly reliable (thanks to its resistance to mechanical disturbances and thanks to its design which resists an interruption in the operation of the circulation pump 10 of a few seconds) and to require little maintenance (thanks to the water recovery system).

APPENDIX

This appendix shows in greater detail the calculation of the V5/V4 ratio for a device according to the invention that was carried out by the inventors; it is also used as an example. In this appendix the parameter is designated by tsafety and the angle α is designated by θ.

The physical parameters that are known and that can be measured are as follows:

Ss Outlet section 15 of the nozzle 4 of concentration

Se Inlet section 14 of the nozzle 4 of concentration

H Height of the nozzle 4 of concentration, from the base to the section Ss

Pelectric Electrical power

In order to limit the phenomenon of cavitation as well as a lack of water in the nozzle 4, the following conditions are set:

Se>>Ss, ideally Se≥3.5 Ss

It is known that the outlet speed of the jet Vjet 17 is linked to the acoustic power of the piezoelectric component 1 as well as to the geometric parameters of the nozzle 4:

Vjet=f(Pacoustic; H; Ss; θ)

If the geometrical parameters H, Ss, θ are set the following is obtained

Vjet=f(Pacoustic; K1) with constant index K1.

In addition it is known that Pacoustic=f(Pelectric; K2) with a constant index K2.

The following is obtained Vjet=f(Pelectric; K1; K2) or

Vjet=f(Pelectric; K3) with a constant index K3.

A description of the operation is provided here in the event of a loss of prime of the circulation pump 10, in particular in order to evaluate the ratio of the volumes of water V5/V4:

The initial conditions are as follows (stationary regime):

System filled with water.

Circulation pump 10 and acoustics (generation of the mist, excitation of the ceramic component 1) operating.

The volumes V1, V2, V3, V4 and V5 are practically constant.

In the event of a loss of prime of the pump 10 due to a disturbance in the suction of the water in the collection reservoir 6, i.e. when the circulation pump 10 can no longer suck the volume V1 and V2 in water, the volume V5 (volume of water higher in the pressurizing chamber 5) has to ensure during a time tsafety the supplying with water of the volume V4 of the nozzle 4.

The following relationship is as such deduced:

$$V5 \geq Qjet \cdot tsafety$$

$$V5 \geq Vjet \cdot Ss \cdot tsafety$$

$$V5 \geq K3 \cdot Pelectric \cdot Ss \cdot tsafety \text{ as } Se \geq 3s,$$

It can also be said that: V5≥[K3·Pelectric·Se·tsafety]/3

A device carried out by the inventors is characterized by the following parameters:

$$S_s = \frac{\pi \cdot d^2}{4} = \frac{\pi \cdot 6^2}{4} \text{ mm}^2$$

with d=6 mm for the diameter of the opening 15 of the nozzle 4.

It is checked that Se>>Ss, $$4 \cdot \frac{\pi \cdot S^2}{4} \gg \frac{z \cdot 6^2}{4}$$

and 100>>36.

We know that K3=0.02 for a nozzle diameter between 4 and 8 mm and θ=10° with H=38 mm (H designates the inside height of the nozzle 4).

In addition, in the example Pelectric=50 W (constant).

If the target tsafety=3 sec is fixed, the following is obtained:

$$V5 \geq K3 \cdot P \text{ electric} \cdot Ss \cdot tsafety \text{ and } V5 \geq 85 \text{ ml.}$$

The volume V5 must therefore be at least 85 ml in order to provide a supplying with water in the volume of the nozzle V4 for 3 seconds.

REFERENCE FIGURES

1 Ceramic piezoelectric component
2 Seal
3 Support for the ceramic component
4 Concentration nozzle
5 Pressurizing chamber
6 Collection reservoir (primary)
7 Tube for guiding the diffusion
8 Chamber 5 filling conduit
9 Water presence sensor
10 Circulation pump
11 Air inlet
12 Nebulization outlet
13 Inlet for water filling
14 Opening for the intake of water of the nozzle
15 Outlet opening of the nozzle
16 Stabilization plates
17 Water jet
18 Micro-droplets of water
19 Mist
20 Opening in the stabilization plate
21 Wall of the nozzle
22 Wall of the pressurizing chamber
23 Base of the nozzle
24 Water presence sensor
25 Discharge opening of the reservoir 6
26 Bottom of the collection reservoir 6
40 Nebulizer device
V1 Volume of water in the reservoir 6
V2 Volume of water in the pump 10
V3 Volume of water in the chamber 5 (lower)
V4 Volume of water in the nozzle 4
V5 Volume of water in the chamber 5 (upper)
Q Flow of water generated by the ceramic component 1

What is claimed is:

1. A nebulizer device, comprising:

a nebulizer nozzle with at least one intake opening for an intake of liquid, at least one outlet opening, a piezoelectric component on a side opposite said at least one outlet opening to emit acoustic waves into the liquid, a transversal section of said nozzle having a progressive narrowing in a direction of said at least one outlet opening, in such a way that, in said nebulizer nozzle, the acoustic waves are focused to create a mist of droplets of said liquid;

a collection reservoir which supplies said nebulizer nozzle with the liquid;

a pump connected to the collection reservoir, and connected said nebulizer nozzle by the at least one intake opening, said circulation pump configured to generate a liquid pressure in said nebulizer nozzle sufficient to maintain a liquid jet emerging via said at least one outlet opening;

a pressurizing chamber through which passes the liquid emerging from the circulation pump before entering said nebulizer nozzle, wherein a first volume of an upper part of the pressurizing chamber at a liquid level is at least twelve times as large as a second volume of the nebulizer nozzle, the first volume being higher than a highest of:

the at least one inlet opening for the intake of water of the highest nozzle, an upper edge of the at least one outlet opening, and a highest point of the piezoelectric component.

2. The nebulizer device of claim 1, wherein the transversal section of said nebulizer nozzle has a narrowing region to focus the acoustic waves on said at least one outlet opening.

3. The nebulizer device of claim 1, wherein a sum of surfaces of the at least one intake opening is at least three times higher than a section of the at least one outlet opening.

4. The nebulizer device of claim 1, wherein a longitudinal axis of said nebulizer nozzle forms an angle of inclination a with respect to the horizontal which is between 5° and 20°.

5. The nebulizer device of claim 1, further comprising at least one stabilization plate of the level of liquid, arranged horizontally, vertically or at an angle, at least one stabilization plate having at least one opening and/or forming at least one opening with at least one other stabilization plate or a wall of said collection reservoir.

6. The nebulizer device of claim 5, wherein said at least one stabilization plate comprises at least two stabilization plates arranged in such a way that the at least one opening is offset in relation to one another.

7. The nebulizer device of claim 1, wherein a bottom of said collection reservoir is inclined in a direction of a discharge opening through which the liquid enters into said circulation pump.

8. The nebulizer device of claim 1, wherein said collection reservoir and said nebulizer nozzle form a block.

9. The nebulizer device of claim 1, further comprising a ventilator to create a flow of air that carries said mist of droplets towards an exterior of said nebulizer device.

10. The nebulizer device of claim 1, further comprising a collection tube to collect a jet of the liquid jet that emerges from the at least one outlet opening, and to empty into said collection reservoir.

11. The nebulizer device of claim 10, wherein said collection tube is passed through by said flow of air that carries said mist of droplets towards an outlet of the collection tube.

12. The nebulizer device of claim 1, further comprising a secondary liquid reservoir connected to the collection reservoir.

13. The nebulizer device of claim 1, further comprising a heater to evaporate any residual liquid in said nebulizer device after the nebulizer device is deactivated.

14. The nebulizer device of claim 1, further comprising at least one detector to detect a lack of liquid and which is combined with a feedback loop in order to cut off or decrease an intensity of the acoustic waves emitted by the piezoelectric component upon detection of a lack of liquid.

15. The nebulizer device of claim 14, wherein said detector comprises a sensor or a plurality of sensors, and which is configured to measure an electrical parameter of the circulation pump.

16. The nebulizer device of claim 15, further comprising a detector of the level of liquid in the collection reservoir.

17. A method for operating a nebulizer device, the method comprising:

permitting a liquid to enter into a collection reservoir of the nebulizer device via an inlet opening;

detecting a level of the liquid in the collection reservoir;

activating a pump connected to the collection reservoir when a detected level of said liquid is at a first predetermined threshold level;

creating, via the pump, a liquid pressure so that the liquid can enter into a nebulizer nozzle, and form a stable jet of the liquid jet to emerge from at least one outlet opening, such that during at least a portion of this time, the liquid is made to enter into the collection reservoir via the inlet opening; and activating a piezoelectric component to emit acoustic waves into the liquid to create a mist of droplets of said liquid, when a detected level of said liquid has reached a second predetermined threshold level.

18. The method of claim 17, wherein first predetermined threshold level and said second predetermined threshold level are the same.

* * * * *